(12) United States Patent
Comins et al.

(10) Patent No.: US 7,501,520 B2
(45) Date of Patent: Mar. 10, 2009

(54) REGIOSELECTIVE HALOGENATION OF NICOTINE AND SUBSTITUTED NICOTINES

(75) Inventors: Daniel L. Comins, Raleigh, NC (US); Florence Fevrier, Cary, NC (US); Emilie Despagnet Smith, Raleigh, NC (US)

(73) Assignee: North Carlina State University, Raleigh, NC (US)

( * ) Notice: Subject to any disclaimer, the term of this patent is extended or adjusted under 35 U.S.C. 154(b) by 0 days.

(21) Appl. No.: 11/623,340

(22) Filed: Jan. 16, 2007

(65) Prior Publication Data

US 2007/0112195 A1    May 17, 2007

Related U.S. Application Data

(62) Division of application No. 11/413,281, filed on Apr. 28, 2006, now Pat. No. 7,179,917, which is a division of application No. 10/926,821, filed on Aug. 26, 2004, now Pat. No. 7,067,672.

(60) Provisional application No. 60/498,046, filed on Aug. 27, 2003.

(51) Int. Cl.
*C07D 401/04* (2006.01)
(52) U.S. Cl. .................... 546/276.4; 546/279.4
(58) Field of Classification Search ............... 546/276.4
See application file for complete search history.

(56) References Cited

U.S. PATENT DOCUMENTS

| 5,594,011 A | 1/1997 | McDonald et al. |
| 5,723,477 A | 3/1998 | McDonald et al. |
| 2005/0113336 A1 | 5/2005 | Comins et al. |
| 2005/0119480 A1 | 6/2005 | Comins et al. |

OTHER PUBLICATIONS

Gros, P., et. al. "nBuLi/Lithium Aminoalkoxide Aggregates: New and Promising Lithiating Agents for Pyridine Derivatives" European Journal of Organic Chemistry 2002, 3375-3383 Published Online: Sep. 30, 2002.*
Mongin et. al. Journal of Organic Chemistry 2004, 69, 6766-6771.*
Clayden, J. Organolithiums: Selectivity for Organic Synthesis 2002, Pergamon: New York, , Chapter 2, p. 50-51; Chapter 3, p. 111-115.*
Anthony B. Eminla and Dietmar Seyferth "The Preparation and Some Reactions of 1,2-Bis (trimethyltin) benzene and Related Compounds" Journal of the American Chemical Society Feb. 15, 1967, 89 (4), 952-959.*
Hansson et. al. Tetrahedron 1982 38, 389-391 (Reaction Diagram also provided).*
Yamamoto, Y.; Akihiko, Y. Heterocycles 1981, 16, 1161-1164.*
Saji, H. et. al. Chemical and Pharmaceutical Bulletin 1997, 45(2), 284-290.*
Gros et al. Lithiation of 2-Heterosubstituted Pyridines with BuLi-LiDMAE: Evidence for Regiospecificity at C-6. *Journal of Organic Chemistry*, 67, 234-237, 2002.
Kondo et al. TMP-Zincate as Highly Chemoselective base for Directed Ortho Metalation. *Journal of the American Chemical Society*, 121, 3539-3540, 1999.
Bleicher, et al. A Practical and Efficient Synthesis of the Selective Neuronal Acetylcholine-Gated Ion Channel Agonist (S)-(-)-5-Ethynyl-3-(1-methyl-2-pyrrolidinyl)pyridine Maleate (SIB-1508Y). *J. Org. Chem.* 63: 1009-1118 (1998).
Brown, et al. A Convenient Synthesis of Dimethyl (Diazomethyl)phosphate (Seyferth/Gilbert Reagent). *J. Org. Chem.* 61:2540-2541 (1996).
Seeman J.I. et al., Nicotine Chemistry: the addition of organlithium reagents to (-)-nicotine. Tetrahedron (1985), vol. 41, No. 3, pp. 595-602.
Comins D.L. and Mantlo N.B. Regioselective addition of nucleophiles to 1-(phenoxycarbonyl)-3-trialkylstannylpyridinium salts. Tetrahedron Letters (1987), vol. 28, No. 7, pp. 759-762.
Wagner F.F. and Comins D.L. Recent advances in the synthesis of nicotine and its derivatives. Tetrahedron (2007), vol. 63, pp. 8065-8082.
Ondachi P.W. and Comins D.L. Synthesis and regioselective substitution of C-6 alkoxy derivatives of (S)-nicotine, Tetrahedron Letters (2008), vol. 49, pp. 569-572.

* cited by examiner

*Primary Examiner*—Rita J Desai
*Assistant Examiner*—David K O'Dell
(74) *Attorney, Agent, or Firm*—Myers Bigel Sibley & Sajovec, P.A.

(57) ABSTRACT

A first aspect of the present invention is a method for of making a compound of Formula Ia or Formula Ib:

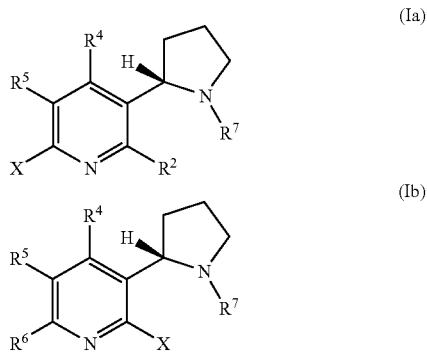

wherein X is halo, by (a) metalating a precursor compound to form an organometallic intermediate, and then reacting the organometallic intermediate with a halogenating agent to produce the compound of Formula Ia or Formula Ib.

15 Claims, No Drawings

REGIOSELECTIVE HALOGENATION OF NICOTINE AND SUBSTITUTED NICOTINES

RELATED APPLICATIONS

This application claims priority to and is a divisional of U.S. patent application Ser. No. 11/413,281 filed Apr. 28, 2006, now U.S. Pat. No. 7,179,917 which is a divisional of parent application Ser. No. 10/926,821 filed Aug. 26, 2004 (now U.S. Pat. No. 7,067,672), which claims the benefit of provisional application Ser. No. 60/498,046 filed Aug. 27, 2003, the disclosures of which are hereby incorporated herein by reference in their entirety.

FIELD OF THE INVENTION

The present invention concerns methods and intermediates useful for the synthesis of compounds active for modulating nicotinic acetylcholine receptors.

BACKGROUND OF THE INVENTION

Acetylcholine receptors are involved in the modulation of a variety of physiological and behavioral functions, including neuroendocrine function, respiration, mood, motor control and function, focus and attention, concentration, memory and cognition, and substance abuse. Ligands for acetylcholine receptors have been demonstrated to have effects on attention, cognition, appetite, substance abuse, memory, extrapyramidal function, cardiovascular function, pain and gastrointestinal motility and function. The distribution of acetylcholine receptors that bind nicotine, i.e., nicotinic acetylcholine receptors, is widespread in the brain. In the periphery, acetylcholine receptors are found in muscle, autonomic ganglia, the gastrointestinal tract and the cardiovascular system (see, e.g., U.S. Pat. No. 5,594,011).

Acetylcholine receptors have been shown to be decreased, among other things, in the brains of patients suffering from Alzheimer's disease, and Parkinson's disease, as well as diseases associated with dementia, motor dysfunction and cognitive impairment. Such correlations between acetylcholine receptors and nervous system disorders suggest that compounds that modulate acetylcholine receptors will have beneficial therapeutic effects for many human nervous system disorders. U.S. Pat. No. 5,594,011 to McDonald et al., assigned to SEBIA Neuroscience, describes compounds such as SIB-1508Y that modulate nicotinic acetylcholine receptors. Such compounds are useful for, among other things, the treatment of Parkinson's disease. See also U.S. Pat. No. 5,723,477 to McDonald et al. Unfortunately, nicotine analogs are difficult compounds to synthesize, and there is a continuing need for new methods of making the same, as well as intermediates useful for the synthesis of nicotine analogs.

Y. Kondo et al., *J Am. Chem. Soc.* 121, 3539-3540 (1999), describe TMP-Zincate as a chemoselective base for directed ortho-metalation of certain aromatic and heteroaromatic compounds, along with the subsequent iodination thereof. P. Gros et al., *J. Org. Chem.* 67, 234-237 (2002), describe the lithiation of 2-heterosubstituted pyridines with BuLi-LiD-MAE. However, neither reference describes or suggests the halogenation of nicotine or nicotine analogs.

SUMMARY OF THE INVENTION

A first aspect of the present invention is a method for of making a compound of Formula Ia:

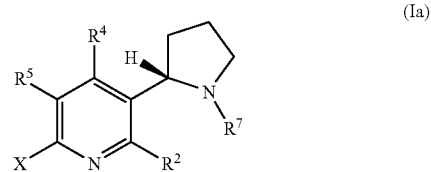

wherein:
$R^2$ is H, alkyl, aryl, alkoxy or halo;
$R^4$ and $R^5$ are H, alkyl or aryl, or $R^4$ is —$SiR^{20}R^{21}R^{22}$, wherein $R^{20}$, $R^{21}$ and $R^{22}$ are each independently alkyl or aryl;
$R^7$ is H, alkyl or aryl; and
X is halo; comprising the steps of:
(a) metalating a compound of Formula II:

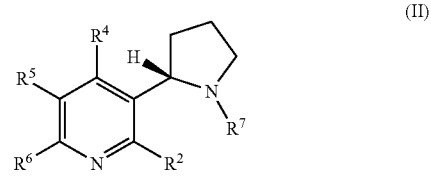

wherein $R^6$ is H, with a metal base complex to form an organometallic intermediate compound; and then
(b) reacting the organometallic intermediate compound with a halogenating agent to produce a compound of Formula Ia.

A second aspect of the present invention is a method of making a compound of Formula Ib:

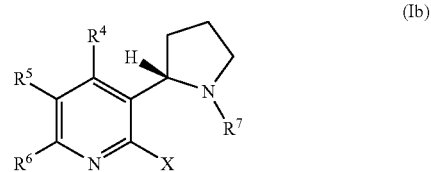

wherein
$R^4$ and $R^5$ are H, alkyl or aryl, or $R^4$ is —$SiR^{20}R^{21}R^{22}$, wherein $R^{20}$, $R^{21}$ and $R^{22}$ are each independently alkyl or ary;
$R^6$ is H, alkyl, aryl, alkoxy or halo;
$R^7$ is H, alkyl or aryl; and X is halo; comprising the steps of:

(a) metalating a compound of Formula II:

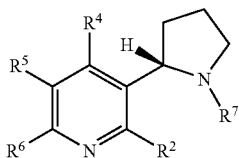

(II)

wherein $R^2$ is H, with a metal base in the presence of a compound of the formula $XSnR^{30}R^{31}R^{32}$, wherein X is halo and $R^{30}$, $R^{31}$ and $R^{32}$ are each alkyl or aryl, to form an organometallic intermediate compound of Formula III:

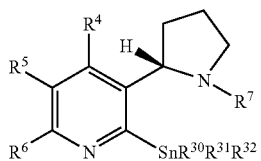

(III)

and then (b) reacting the organometallic intermediate compound of Formula III with a halogenating agent to produce a compound of Formula Ib.

A third aspect of the present invention is organometallic intermediate compounds such as compound of Formula III as described above, which intermediate compounds are useful as compounds having acetylcholine receptor modulating activity, and are useful as intermediates for making compounds having acetylcholine receptor modulating activity, all as described in greater detail above.

DETAILED DESCRIPTION OF THE PREFERRED EMBODIMENTS

"Alkyl" as used herein refers to straight or branched chain or cyclo alkyl groups having in the range of about 1 up to 12 carbon atoms. "Lower alkyl" refers to straight or branched chain alkyl groups having in the range of about 1 up to 4 carbon atoms. Alkyl and loweralkyl may be substituted or unsubstituted unless specified otherwise herein; "substituted alkyl" refers to alkyl or lower alkyl groups further bearing one or more substituents such as hydroxy, alkoxy (of a lower alkyl group), aryl, mercapto (of a lower alkyl group), halogen, trifluoromethyl, cyano, nitro, amino, carboxyl, carbamate, sulfonyl, sulfonamide, and the like. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like.

"Alkoxy" as used herein refers to a compound of the formula RO—, where R is alkyl or loweralkyl (which may be substituted or unsubstitued unless specified otherwise) as given above.

"Alkenyl" refers to straight or branched chain hydrocarbyl groups such as alkyl or loweralkyl groups as described above (and which may be substituted or unsubstituted unless specified otherwise) and having at least one carbon-carbon double bond.

"Alkynyl" refers to straight or branched chain hydrocarbyl radicals such as alkyl or loweralkyl groups as described above (and which may be substituted or unsubstituted unless specified otherwise) and having at least one carbon-carbon triple bond.

"Aryl," as used herein, refers to a monocyclic carbocyclic ring system or a bicyclic carbocyclic fused ring system having one or more aromatic rings. Examples of aryl include but are not limited to azulenyl, indanyl, indenyl, naphthyl, phenyl, tetrahydronaphthyl, and the like. The aryl groups may be substituted or unsubstituted unless specified otherwise and when substituted can for example be substituted with 1, 2, 3, 4, or 5 substituents independently selected from alkyl, alkenyl, alkenyloxy, alkoxy, alkoxyalkoxy, alkoxycarbonyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR'R" (wherein R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl).

"Halo" refers to fluoro, chloro, bromo or iodo.

"Halogenating agent" as used herein may be any suitable halogenating agent, including but not limited to $I_2$, $C_2Cl_6$, N-bromosuccinimide, $Br_2$, N-iodosuccinimide, $CCl_4$, 1,3-dichloro-5,5-dimethylhydantoin, etc.

The disclosures of all United States patent references cited herein are to be incorporated herein by reference in their entirety.

Compounds of Formula II, used as starting materials herein, can be produced in accordance with known techniques or variations thereof that will be apparent to persons skilled in the art, including but not limited to the techniques set forth in U.S. Pat. No. 5,594,011 to McDonald et al., and U.S. Pat. No. 5,723,477 to McDonald et al.

A first aspect of the present invention is, as noted above, a method of making a compound of Formula Ia:

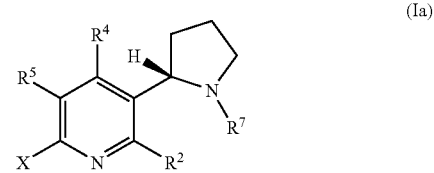

(Ia)

wherein:

$R^2$ is H, alkyl, aryl, alkoxy or halo (preferably H or alkyl; most preferably H);

$R^4$ and $R^5$ are H, alkyl or ary (preferably H or alkyl), or $R^4$ is —$SiR^{20}R^{21}R^{22}$, wherein $R^{20}$, $R^{21}$ and $R^{22}$ are each independently alkyl or aryl (preferably alkyl, most preferably methyl);

$R^7$ is H, alkyl or aryl (preferably H or alkyl, most preferably methyl); and

X is halo, preferably chloro.

The method comprises the steps of (a) metalating a compound of Formula II:

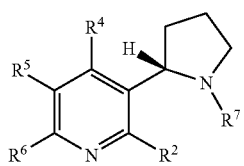

(wherein $R^2$, $R^4$, $R^5$ and $R^7$ are as given above, and $R^6$ is H) with a metal base complex to form an organometallic intermediate compound; and then (b) reacting the organometallic intermediate compound with a halogenating agent to produce a compound of Formula Ia.

The metal base may be an alkyllithium base, an example of which is the basic reagent composed of BuLi and $Me_2N(CH_2)_2OLi$ known as BuLi-LiDMAE and described in, for example, P. Gros, *J. Org. Chem.* 67, 234-237 (2002) and sometimes referred to as Base A herein. Another suitable base for carrying out the methods of the present invention is lithium di-tert-butyltetramethylpiperidinozincate (TMP-zincate), described in, for example, Y. Kondo, *J. Am. Chem. Soc.* 121, 3539-3540, and sometimes referred to as Base B herein.

Reactions of the present invention may be carried out in any suitable organic solvent, with the particular solvent chosen depending in part on the base chosen for the reaction. For example, reactions utilizing Base A are preferably carried out in a nonpolar aprotic solvent such as hexane. Reactions utilizing base B are preferably carried out in an etherial solvent such as tetrahydrofuran. The reactions may be conveniently carried out as "one pot" reactions if desired. The time and temperatures of the reactions are not critical, but may for example be from −80° C. to 100° C., and from 1 to 24 hours in duration.

Another aspect of the present invention is a method of making a compound of Formula Ib:

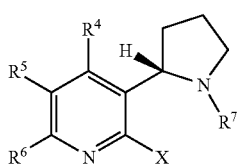

wherein $R^4$ and $R^5$ are H, alkyl or aryl (preferably H or alkyl, most preferably H), or $R^4$ is $-SiR^{20}R^{21}R^{21}$, wherein $R^{20}$, $R^{21}$ and $R^{22}$ are each independently alkyl or ary (preferably alkyl, most preferably methyl);

$R^6$ is H, alkyl, aryl, alkoxy or halo (preferably H or alkyl, most preferably H);

$R^7$ is H, alkyl or aryl (preferably H or alkyl, most preferably methyl); and

X is halo, preferably chloro.

The method comprises the steps of (a) metalating a compound of Formula II:

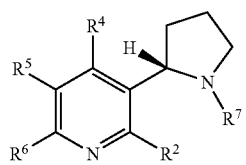

wherein $R^2$ is H, with a base in the presence of a compound of the formula $XSnR^{30}R^{31}R^{32}$, wherein X is halo (preferably chloro) and $R^{30}$, $R^{31}$ and $R^{32}$ are each alkyl or aryl (preferably alkyl, most preferably cyclohexyl), to form an organometallic intermediate compound of Formula III:

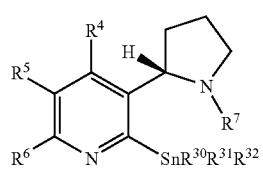

and then (b) reacting the organometallic intermediate compound of Formula III with a halogenating agent in an aprotic organic solvent such as chloroform as described above to produce a compound of Formula Ib. The base utilized in step (a) is preferably a strong base such as lithium tetramethylpiperidide, sometimes referred to as Base C herein. The compound of formula $XSnR^{30}R^{31}R^{32}$ is preferably tricyclohexyltin chloride. Compounds of Formula III may be isolated if desired. Solvents and temperatures for Base C may be the same as described for Base B above, e.g., tetrahydrofuran, and temperatures of −80° C. to 100° C.

Compounds of Formula Ia and Formula Ib are useful as acetylcholine receptor modulating compounds and are useful as pharmacologically and pharmaceutically active compounds, including compounds useful for the treatment of neurological disorders such as Parkinson's disease, Alzheimer's disease, motor dynsfunction and cognitive impairment in human and animal subjects, as compounds for use as an alternative to nicotine as an aid to smoking cessation programs, as insecticides, etc. Compounds of Formula III are useful as intermediates for making compounds of Formula Ib.

The present invention is explained in greater detail in the following non-limiting Examples.

EXAMPLES 1-4

Regioselective Halogenation of (S)-Nicotine

Base A:

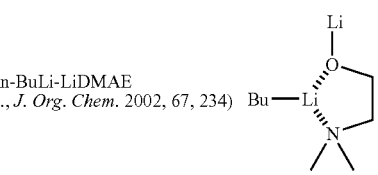

n-BuLi-LiDMAE
(Y. Fort et. al., *J. Org. Chem.* 2002, 67, 234)

-continued

Base B:

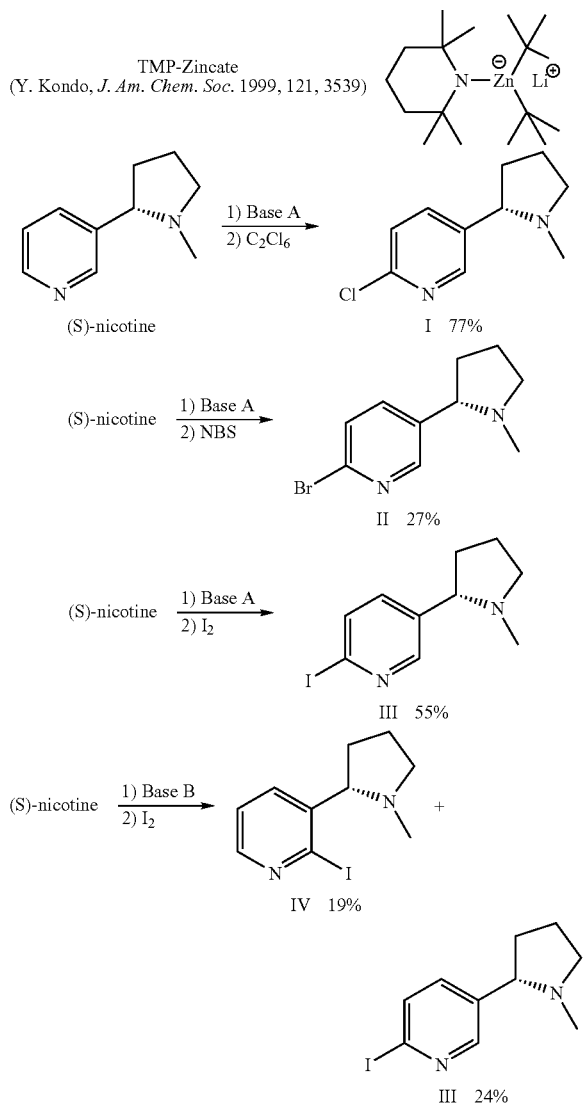

Example 1

Preparation of 2-Chloro-5-(1-methyl-pyrrolidin-2-yl)pyridine (I)

A solution of 2-(dimethylamino)ethanol (300 μL, 3.0 mmol, 3.0 eq) in hexane (2 mL) was cooled to 0° C., and treated dropwise with n-butyllithium (5.4 mmol, 5.4 eq) under an argon atmosphere. After 30 min at 0° C., the mixture was cooled to −20° C. and (S)-nicotine (160 μL, 1.0 mmol, 1.0 eq) was added dropwise. After 1 h of stirring, a brown solution was observed. The mixture was cooled to −78° C. and treated dropwise with a solution of hexachloroethane in toluene (2.0 mL). After 1 h at −78° C., the mixture was hydrolyzed at −78° C. with a saturated solution of sodium bicarbonate (1 mL) and then warmed to room temperature. The aqueous layer was extracted with dichloromethane (10 mL). The combined organic layers were dried over magnesium sulfate. After evaporation of solvents, the crude product was purified by radial plc (1% Et$_3$N/hexane as eluent) to give 151 mg (77%) of pure product as a yellow oil. IR (thin film, CHCl$_3$, NaCl) 2961, 2923, 2865, 2846, 1452, 1019 cm$^{-1}$. $^1$H NMR (400 MHz, CDCl$_3$) δ 8.24 (d, 1H, J=2.4 Hz), 7.62 (dd, 1H, J=2.4 Hz, J=8 Hz), 7.23 (d, 1H, J=8 Hz), 3.14 (dt, 1H, J=2 Hz, J=8 Hz), 3.02 (t, 1H, J=8 Hz), 2.1-2.4 (m, 2H), 2.09 (s, 3H), 1.87-1.89 (m, 1H), 1.73-1.79 (m, 1H), 1.55-1.65 (m, 1H). $^{13}$C NMR (100 MHz, CDCl$_3$), δ 150.23, 149.35, 138.23, 138.06, 124.47, 68.19, 57.12, 40.52, 25.51, 22.79. HRMS Calcd for C$_{10}$H$_{13}$ClN$_2$ 196.0767, found 196.0754. [α]$^{25}$$_D$−35 (c 10.0, CHCl$_3$). Compound I is a known compound, see: Schmidt, B.; Neitemeier, V. Synthesis, 1997, 42-44.

Example 2

6-Bromonicotine (II)

A solution of 2-(dimethylamino)ethanol (300 μL, 3.0 mmol, 3.0 eq) in hexane (2 mL) was cooled to 0° C., and treated dropwise with n-butyllithium (5.4 mmol, 5.4 eq) under an argon atmosphere. After 30 min at 0° C., the mixture was cooled down to −20° C. and (S)-nicotine (160 μL, 1.0 mmol, 1.0 eq) was added dropwise. After 1 h of stirring, a brown solution was observed. The mixture was cooled to −78° C. and treated dropwise with a solution of N-bromosuccinimide (710 mg, 4.0 mmol, 4.0 eq) in toluene (2 mL). After 1 h at −78° C., the mixture was hydrolyzed at -78° C. with a saturated solution of sodium bicarbonate (1 mL) and then warmed to room temperature. The aqueous layer was extracted with dichloromethane (10 mL). The combined organic layers were dried over magnesium sulfate. After evaporation of solvents, the crude product was purified by radial plc (1% Et$_3$N/hexanes as eluent) to give 66 mg (27%) of product as a brown oil. IR (CDCl$_3$): 2968, 2943, 2876, 2840, 2779, 1578, 1561, 1450, 1394, 1327, 1085, 1044, 1019 cm$^{-1}$; $^1$H NMR (300 MHz, CDCl$_3$) δ 8.27 (d, 1H, J=2.0 Hz), 7.57 (dd, 1H, J=8.4 Hz, J=2.0 Hz), 7.43 (d, 1H, J=8.4 Hz), 3.22 (t, 1H, J=8.0 Hz), 3.05 (t, 1H, J=8.0 Hz), 2.33-2.14 (m, 2H), 2.14 (s, 3H), 2.00-1.92 (m, 1H), 1.92-1.79 (m, 1H), 1.79-1.64 (m, 1H) ; $^{13}$C NMR (100 MHz, CDCl$_3$) δ 150.0, 140.8, 138.7, 137.9, 128.3, 68.3, 57.2, 40.6, 35.5, 22.9; HRMS Calcd for C$_{10}$H$_{13}$BrN$_2$: 241.0340. Found 241.0349; [α]$^{25}$$_D$−135 (c 1.5, CH$_2$Cl$_2$).

Example 3

6-Iodonicotine (III)

A solution of 2-(dimethylamino)ethanol (300 μL, 3.0 mmol, 3.0 eq) in hexane (2 mL) was cooled to 0° C., and treated dropwise with n-butyllithium (5.4 mmol, 5.4 eq) under an argon atmosphere. After 30 min at 0° C., the mixture was cooled down to −20° C. and (S)-nicotine (160 μL, 1.0 mmol, 1.0 eq) was added dropwise. After 1 h of stirring, a brown solution was observed. The mixture was cooled to −78° C. and treated dropwise with a solution of iodine (1.015 g, 4.0 mmol, 4.0 eq) in toluene (2.0 mL). After 1 h at −78° C., the mixture was hydrolyzed at −78° C. with a saturated solution of sodium bicarbonate (1 mL) and then warmed to room temperature. The aqueous layer was extracted with dichloromethane (10 mL). The combined organic layers were dried over magnesium sulfate. After evaporation of solvents, the crude product was purified by radial plc (1% Et$_3$N/hexane as eluent) to give 157 mg (55%) of product as a yellow oil. IR (CDCl$_3$): 2966, 2937, 2830, 2779, 1559, 1537, 1453, 1394, 1453, 1394, 1354, 1218, 1057, 850 cm$^{-1}$; $^1$H NMR (300 MHz, CDCl$_3$) δ 8.60 (s, 1H), 8.04 (d, 1H, J=5.4 Hz), 7.70 (d, 1H, J=5.4 Hz), 3.39 (t, 1H, J=6.6 Hz), 3.15 (t, 1H, J=6.6 Hz), 2.38 (m, 2H), 2.24 (s, 3H), 1.2-2.0 (m, 3H) ; $^{13}$C NMR (100 MHz, CDCl$_3$) δ 149.8, 149.4, 148.4, 135.9, 134.3, 72.5, 57.0, 40.8, 33.9, 22.9; HRMS Calcd for C$_{10}$H$_{13}$IN$_2$: 289.0202. Found 289.0200; $[α]^{25}_D$–120 (c 4.2, CH$_2$Cl$_2$).

Example 4

2-Iodonicotine (IV) and 6-Iodonicotine (III)

Under an atmosphere of argon, 2,2,6,6-tetramethylpiperidine (310 μL, 2.2 mmol, 1.1 eq) in dry tetrahydrofuran (5 mL) was cooled to –78° C. and treated with n-butyllithium (2.0 mmol, 1.0 eq). The solution mixture was stirred at 0° C. for 30 min. After 30 min at 0° C., the solution mixture was cooled down to –78° C. and treated with di-tert-butylzinc (2.4 mmol, 1.2 eq) prepared from zinc chloride (4.8 mL, 0.5 M in THF, 2.4 mmol) and t-butyllithium (4.8 mmol, 2.4 eq). The mixture was then stirred at room temperature for 1 h. (S)-Nicotine was added dropwise at room temperature and stirred overnight. Iodine (2.03 g, 8.0 mmol, 4.0 eq) was added to the mixture The flask was wrapped by aluminum foil to protect the reaction from the light. The reaction was quenched with 1.0 mL of a saturated aqueous solution of sodium carbonate. The aqueous layer was extracted with methylene chloride, and the combined organic layers were dried over magnesium sulfate. The solvent was removed by evaporation to afford a yellow oil. The product was purified by radial plc using 1% TEA/hexanes as an eluent. 2-Iodonicotine was obtained in a 19% yield (107 mg) as a brown oil, and 6-Jodonicotine was obtained in a 24% yield (139 mg) as a white solid. 2-Iodonicotine: IR (CDCl$_3$) 2965, 2940, 2778, 1568, 1550, 1446, 1395, 1330, 1034, 805 cm$^{-1}$; $^1$H NMR (300 MHz, CDCl$_3$) δ 8.20 (dd, 1H, J=4.2 Hz, J=1.8 Hz), 7.73 (dd, 1H, J=7.8 Hz, J=1.8 Hz), 7.23 (dd, 1H, J=7.8 Hz, J=4.2 Hz, Hz), 3.33 (t, 1H, J=8.4 Hz), 3.23 (t, 1H, J=8.4 Hz), 2.40-2.20 (m, 2H), 2.20 (t, 3H), 2.00-1.35(m, 3H); $^{13}$C NMR (100 MHz, CDCl$_3$) δ 150.7, 149.4, 137.1, 135.9, 123.7, 72.4, 57.1, 40.7, 33.9, 23.0; HRMS Calcd for C$_{10}$H$_{13}$IN$_2$: 289.0202. Found 289.0203; $[α]^{25}_D$–126 (c 4.5, CH$_2$Cl$_2$). 6-Iodonicotine: mp 97-98° C.; IR (CDCl$_3$) 2966, 2937 2830, 2779, 1559, 1537, 1453, 1394, 1453, 1394, 1354, 1218, 1057, 850 cm$^{-1}$; $^1$H NMR (300 MHz, CDCl$_3$) δ 8.60 (s, 1H), 8.04 (d, 1H, J=5.4 Hz), 7.70 (d, 1H, J=5.4 Hz), 3.39 (t, 1H, J=6.6 Hz), 3.15 (t, 1H, J=6.6 Hz), 2.38 (m, 2H), 2.24 (s, 3H), 1.2-2.0 (m, 3H); $^{13}$C NMR (100 MHz, CDCl$_3$) δ 149.8, 149.4, 148.4, 135.9, 134.3, 72.5, 57.0, 40.8, 33.9, 22.9; HRMS Calcd for C$_{10}$H$_{13}$IN$_2$: 289.0202. Found 289.0200; $[α]^{25}_D$–120 (c 4.2, CH$_2$Cl$_2$).

EXAMPLES 5-6

Regioselective Halogenation of (S)-Nicotine

Base C:

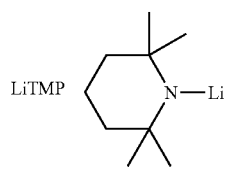

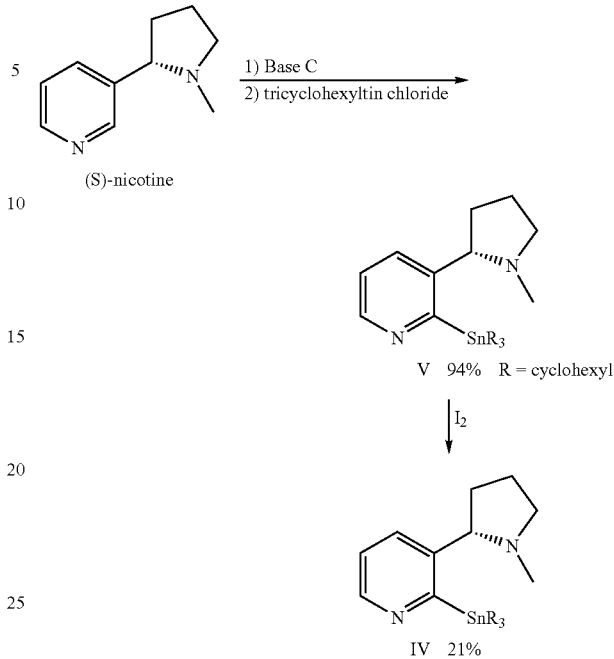

Example 5

3-(1-methylpyrrolidin-2-yl)-2-tricyclohexylstannanyl)pyridine (V)

(S)-Nicotine (160 μL, 1.0 mmol, 1.0 eq) was added at –78° C. to a solution containing both the base, lithium tetramethylpiperidide (510 μL, 3.0 mmol, 3.0 eq) and tricyclohexylchlorotin (810 mg, 2.0 mmol, 2.0 eq). After 1 h at –78° C., the mixture was stored at –25° C. in a freezer overnight. The hydrolysis was performed at –25° C. with 1.0 mL of saturated aqueous solution of sodium bicarbonate. The aqueous layer was extracted with methylene chloride (2×10 mL). The combined organic layers were dried over magnesium sulfate. The solvent was removed by evaporation under reduced pressure to afford a light-yellow oil. The product was purified by radial plc (1% Et$_3$N/hexanes as eluent) to afford 485 mg (92% yield) of a white solid. mp 122-123° C.; IR (CDCl$_3$) 2916, 2845, 2776, 1445, 1169, 1049, 991 cm$^{-1}$; $^1$H NMR (300 MHz, CDCl$_3$) δ 8.60 (dd, 1H, J=4.4 Hz, J=2.0 Hz), 7.69 (dd, 1H, J=8.0 Hz, J=2.0 Hz), 7.10 (dd, 1H, J=8.0 Hz, J=4.4 Hz), 3.26 (t, 1H, J=7.5 Hz), 3.04 (t, 1H, J=7.5 Hz), 2.34 (q, 1H, J=9.0 Hz), 2.29-2.16 (m, 1H), 2.16 (s, 3H), 1.92-1.60 (m, 21H), 1.35-1.20 (m, 12H); $^{13}$C NMR (100 MHz, CDCl$_3$) δ 174.2, 149.3, 146.8, 132.2, 122.2, 70.8, 57.1, 40.4, 36.8, 32.5, 29.7, 29.5, 27.7, 22.8; HRMS Calcd for C$_{28}$H$_{46}$N$_2$Sn: 531.2761. Found 531.2780; $[α]^{25}_D$–74 (c 2.8, CH$_2$Cl$_2$).

Example 6

2-Iodonicotine (IV)

A solution of iodine (0.181 mmol, 46 mg, 4.2 eq) in anhydrous chloroform was added at room temperature to a solution of 3-(1-methylpyrrolidin-2-yl)-2-(tricyclohexylstannanyl)-pyridine (0.043 mmol, 23 mg, 1.0 eq). The reaction was stirred at room temperature for 24 h. A saturated aqueous solution of sodium thiosulfate (0.5 mL) and a saturated aqueous solution of sodium bicarbonate (1.0 mL) were added to the mixture. The aqueous layer was extracted with dichloromethane (10 mL). The combined organic layers were dried over magnesium sulfate. The solvent was removed by evaporation. The product was purified by radial plc (1% Et$_3$N/ hexanes, then 1% TEA/5% EtOAc/hexanes as eluents) to afford 3 mg (21%) of product as a brown oil. IR (CDCl$_3$) 2965, 2940, 2778, 1568, 1550, 1446, 1395, 1330, 1034, 805 cm$^{-1}$; $^1$H NMR (300 MHz, CDCl$_3$) δ 8.20 (dd, 1H, J=4.2 Hz, J=1.8 Hz), 7.73 (dd, 1H, J=7.8 Hz, J=1.8 Hz), 7.23 (dd, 1H, J=7.8 Hz, J=4.2 Hz), 3.33 (t, 1H, J=8.4 Hz), 3.23 (t, 1H, J=8.4 Hz), 2.40-2.20 (m, 2H), 2.20 (t, 3H), 2.00-1.35 (m, 3H); $^{13}$C NMR (100 MHz, CDCl$_3$) δ 150.7, 149.4, 137.1, 135.9, 123.7, 72.4, 57.1, 40.7, 33.9, 23.0; HRMS Calcd for C$_{10}$H$_{13}$IN$_2$: 289.0202. Found 289.0203; [α]$^{25}_D$ –126 (c 4.5, CH$_2$Cl$_2$).

EXAMPLES 7-9

Halogenation of Substituted Nicotines using BuLi-LiDMAE

Example 7

Preparation of 2-chloro-5-(1-methylpyrrolidin-2-yl)-4-trimethylsilanylpyridine (VI)

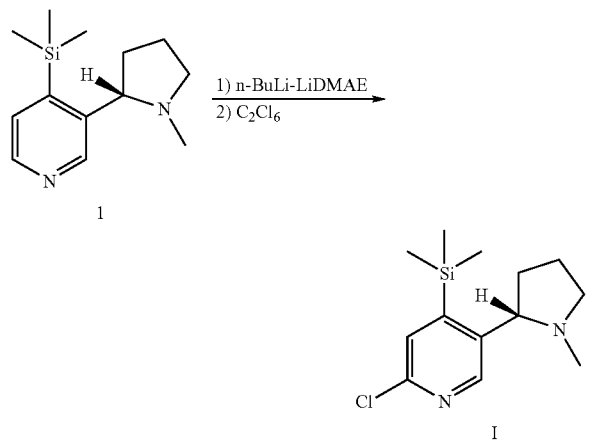

A solution of 2-dimethylaminoethanol (0.57 mL, 5.7 mmol) in hexane (7 mL) was cooled to 0° C. and treated with n-butyllithium (5.2 mL, 11.4 mmol). After 30 min at 0° C., a solution of 4-(trimethylsilanyl) nicotine (1) (0.4461 g, 1.9 mmol) in hexane (3.5 mL) was added dropwise and the mixture was stirred at 0° C. for 1.5 h. It was then cooled to –78° C. and a solution of hexachloroethane (1.8 g, 7.6 mmol) in hexane (5 mL) was added dropwise. The reaction mixture was stirred at –78° C. for 1 h and then allowed to warm to RT over 20 min. The hydrolysis was then performed at 0° C. with water (10 mL). The aqueous layer was extracted with ether (2 times). The combined organic layers were dried over K$_2$CO$_3$. The solvent was removed under reduced pressure and the crude material was purified by RPLC (hexanes) to afford 0.2707 g (53%) of 2-chloro-5-(1-methyl-pyrrolidin-2-yl)-4-trimethylsilanyl-pyridine (VI) as a yellow oil. IR (thin film, neat, NaCl): 2956, 2779, 1252, 1119, 1074, 840 cm$^{-1}$. $^1$H NMR (300 MHz, CDCl$_3$): δ 8.63 (s, 1H), 7.27 (s, 1H), 3.33-3.22 (m, 2H), 2.33-1.61 (m, 8H), 0.35 (s, 9H). $^{13}$C NMR (100 MHz, CDCl$_3$): δ 159.29, 152.05, 149.41, 148.47, 128.10, 126.76, 68.06, 56.80, 40.32, 36.61, 22.74, 0.56, 0.28. HRMS Calcd for C$_{13}$H$_{21}$N$_2$ClSi: 268.1163 [M]$^+$. Found: 268.1139 [M]$^+$. [α]$^{24}_D$ –101.7 (c=14, CH$_2$Cl$_2$).

Example 8

Preparation of 2-chloro-4-(dimethyl-phenyl-silanyl)-5-(1-methyl-pyrrolidin-2-yl)-pyridine (VII)

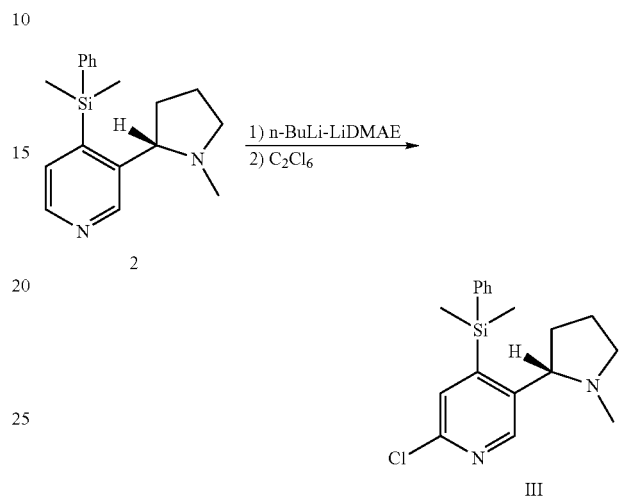

Same as for the preparation of 2-chloro-5-(1-methyl-pyrrolidin-2-yl)-4-trimethylsilanyl-pyridine (VI) using 0.4371 g (1.47 mmol) of 4-(dimethyl-phenyl-silanyl)-3-(1-methyl-pyrrolidin-2-yl)-pyridine (2), 4.41 mL (8.82 mmol) of n-BuLi, 0.44 mL (4.41 mmol) of dimethylamino ethanol and 1.39 g (5.88 mmol) of C$_2$Cl$_6$. Yield: 0.2092 g (43%) of 2-chloro-4-(dimethyl-phenyl-silanyl)-5-(1-methyl-pyrrolidin-2-yl)-pyridine (VII) as a yellow oil. IR (thin film, neat, NaCl): 2956, 2782, 1567, 1451, 1428, 1361, 1252, 1119, 816 cm$^{-1}$. $^1$H NMR (400 MHz, CDCl$_3$): δ 8.60 (s, 1H), 7.62 (s, 1H), 7.45-7.32 (m, 6H), 3.15-3.09 (m, 2H), 1.89-1.25 (m, 8 H), 0.63 (s, 6H). $^{13}$C NMR (100 MHz, CDCl$_3$): δ 159.47, 148.75, 134.20, 129.51, 128.08, 127.65, 68.56, 56.78, 40.11, 38.08, 35.94, 32.94, 32.47, 22.86, 22.67, 14.19, –0.92, –0.97. HRMS Cacd for C$_{18}$H$_{23}$N$_2$ClSi: 331.1397 [M+H]$^+$. Found: 331.1397 [M+H]$^+$. [α]$^{25}_D$ –84 (c=6.7, CH$_2$Cl$_2$).

Example 9

Preparation of 2-iodo-5-(1-methyl-pyrrolidin-2-yl)-4-trimethylsilanyl-pyridine (VIII):

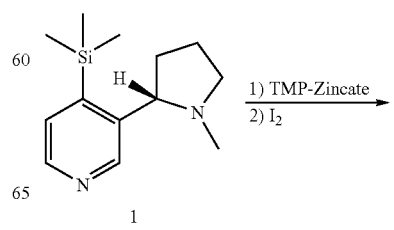

-continued

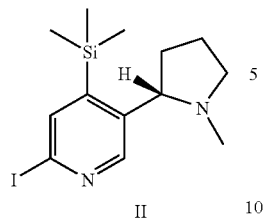

Under Ar atmosphere 2,2,6,6-tetramethylpiperidine (0.51 mL, 3.04 mmol) was added to dry THF (6 mL) and the mixture was cooled to −78° C. n-Butyllithium was slowly added to the mixture at −78° C. and the mixture was stirred at 0° C. for 30 min. In a separate flask, a solution of zinc chloride in THF (6.62 mL, 3.31 mmol) was cooled to −78° C. and tert-butyllithium (3.9 mL, 6.62 mmol) was slowly added. The mixture was stirred at −78° C. for 1 h. The solution of di (tert-butyl) zinc prepared was then introduced via a double tipped needle into the solution of TMP-lithium cooled at −78° C. The mixture was allowed to warm to RT for 1 h. To that solution was added at RT a solution of 4-(trimethylsilanyl) nicotine (1) (0.3238 g, 1.38 mmol) in THF (4 mL). The mixture was stirred at RT overnight and the solution turned brown orange. A solution of iodine (1.65 g, 5.52 mmol) was slowly added at 0° C. and the reaction mixture was allowed to warm to RT for 7 h. A saturated aqueous solution of NaHCO$_3$ (2 mL) was the introduced. The aqueous layer was extracted with ether (3 times). The combined organic layers were washed with water and dried over K$_2$CO$_3$. The solvent was removed under reduced pressure and the crude material was purified by RPLC (hexanes) to afford 0.0531 g (15%) of 2-iodo-5-(1-methyl-pyrrolidin-2-yl)-4-trimethylsilanyl-pyridine (VIII) as a yellow oil and 0.2 g (62%) of SM. IR (thin film, neat, NaCl): 2954, 1446, 1251, 1092, 840 cm$^{-1}$. $^1$H NMR (300 MHz, CDCl$_3$): δ 8.59 (s, 1H), 7.62 (s, 1H), 3.28-3.23 (m, 2H), 2.30-1.62 (m, 8H), 0.34 (s, 9H). $^{13}$C NMR (100 MHz, CDCl$_3$): δ 151.56, 150.87, 144.29, 138.80, 117.14, 68.34, 56.95, 40.49, 36.71, 22.89, 0.44. HRMS Cacd for C$_{13}$H$_{21}$N$_2$ISi: 361.0597 [M+H]$^+$. Found: 361.0611 [M+H]$^+$. [α]$^{24}_D$ −88.68 (c=2.5, CH$_2$Cl$_2$)

The foregoing is illustrative of the present invention, and is not to be construed as limiting thereof. The invention is defined by the following claims, with equivalents of the claims to be included therein.

That which is claimed is:
1. A method of making a compound of Formula Ib:

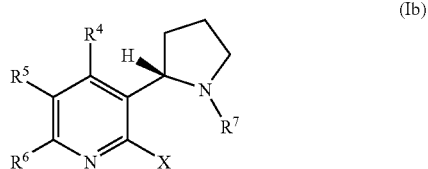

wherein
R$^4$ and R$^5$ are H, alkyl or aryl, or R$^4$ is —SiR$^{20}$, R$^{21}$ R$^{22}$, wherein R$^{20}$, R$^{21}$ and R$^{22}$ are each independently alkyl or aryl;
R$^6$ is H, alkyl, aryl or halo;
R$^7$ is H, alkyl or aryl; and X is halo; comprising the steps of:
(a) metalating a compound of Formula II:

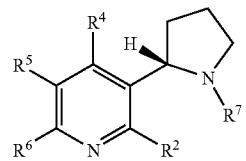

wherein R$^2$ is H, with lithium tetramethylpiperidide in the presence of a compound of the formula X'SnR$^{30}$R$^{31}$R$^{32}$, wherein X' is halo and R$^{30}$, R$^{31}$ and R$^{32}$ are each alkyl or aryl, to form an organometallic intermediate compound of Formula III:

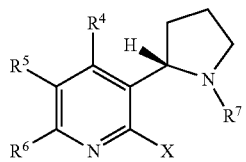

and then
(b) reacting said organometallic intermediate compound of Formula III with a halogenating agent to produce a compound of Formula Ib.

2. The method of claim 1, wherein said halogenating agent is selected from the group consisting of I$_2$, N-bromosuccinimide, Br$_2$, N-iodosuccinimide, and 1,3-dichloro-5,5-dimethylhydantoin.

3. The method of claim 1, wherein R$^6$ is H.

4. The method of claim 1, wherein R$^4$ and R$^5$ are H.

5. The method of claim 1, wherein R$^7$ is methyl.

6. The method of claim 1, wherein said compound of Formula II is (S)-nicotine.

7. The method of claim 1, wherein X is chloro.

8. The method of claim 1, wherein R$^{30}$, R$^{31}$ and R$^{32}$ are each cyclohexyl.

9. The method of claim 1, wherein said compound of the formula X'SnR$^{30}$R$^{31}$R$^{32}$ is tricyclohexyltin chloride.

10. A method of making a compound of Formula Ib:

wherein
R[4] and R[5] are each H, alkyl or aryl, wherein R[20], R[21] and R[22] are each independently alkyl or aryl;
R[6] is H, alkyl or aryl;
R[7] is H, alkyl or aryl; and
X is halo; comprising the steps of:
(a) metalating a compound of Formula II:

(II)

wherein R[2] is H, with lithium tetramethylpiperidide in the presence of a compound formula X'SnR[30]R[31]R[32], wherein X' is halo and R[30], R[31] and R[32] are each alkyl or aryl, to form an organometallic intermediate compound of Formula III:

(III)

and then
(b) reacting said organometallic intermediate compound of Formula III with a halogenating agent to produce said compound of Formula Ib.

11. The method of claim 10, wherein said halogenating agent is selected from the group consisting of $I_2$, N-bromosuccinimide, $Br_2$, N-iodosuccinimide, and 1,3-dichloro-5,5-dimethylhydantoin.

12. The method of claim 10, wherein R[6] is H.

13. The method of claim 10, wherein R[4] and R[5] are H.

14. The method of claim 10, wherein R[7] is methyl.

15. The method of claim 10, wherein said compound of Formula II is (S)-nicotine.

* * * * *

UNITED STATES PATENT AND TRADEMARK OFFICE
CERTIFICATE OF CORRECTION

PATENT NO. : 7,501,520 B2 Page 1 of 1
APPLICATION NO. : 11/623340
DATED : March 10, 2009
INVENTOR(S) : Comins et al.

It is certified that error appears in the above-identified patent and that said Letters Patent is hereby corrected as shown below:

Column 10, Lines 20-25: Please correct "SnR$_3$" in the structure to read -- 1 --

Signed and Sealed this

Nineteenth Day of May, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,501,520 B2 | Page 1 of 1 |
| APPLICATION NO. | : 11/623340 | |
| DATED | : March 10, 2009 | |
| INVENTOR(S) | : Comins et al. | |

It is certified that error appears in the above-identified patent and that said Letters Patent is hereby corrected as shown below:

Column 10, Lines 20-25: Please correct "SnR$_3$" in the structure to read -- I --

This certificate supersedes the Certificate of Correction issued May 19, 2009.

Signed and Sealed this

Seventh Day of July, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,501,520 B2  
APPLICATION NO. : 11/623340  
DATED : March 10, 2009  
INVENTOR(S) : Comins et al.

Page 1 of 1

It is certified that error appears in the above-identified patent and that said Letters Patent is hereby corrected as shown below:

In the Specification:
Column 1, Line 16: Please add the following Government Support statement immediately under the Related Applications paragraph:

GOVERNMENT SUPPORT STATEMENT

This invention was made with government support under grant number GM034442 awarded by the National Institutes of Health. The government has certain rights to this invention.

Signed and Sealed this
Nineteenth Day of July, 2016

Michelle K. Lee
*Director of the United States Patent and Trademark Office*